(12) United States Patent
Pan et al.

(10) Patent No.: US 11,918,635 B2
(45) Date of Patent: Mar. 5, 2024

(54) METHOD AND PLATFORM FOR DETECTING IMMUNOGENICITY OF TUMOR NEOANTIGEN

(71) Applicants: NeoCura Bio-Medical Technology Co., Ltd, Shenzhen (CN); Beijing Neocurna Biotechnology corporation, Beijing (CN); Shenzhen Neocurna Biotechnology corporation, Shenzhen (CN)

(72) Inventors: Youdong Pan, Shenzhen (CN); Qi Song, Shenzhen (CN); Ji Wan, Shenzhen (CN); Jun-Yuan Huang, Shenzhen (CN); An Xiao, Shenzhen (CN); Gang Liu, Shenzhen (CN); Ying Wen, Shenzhen (CN)

(73) Assignees: NeoCura Bio-Medical Technology Co., Ltd, Shenzhen (CN); Beijing Neocurna Biotechnology corporation, Beijing (CN); Shenzhen Neocurna Biotechnology corporation, Shenzhen (CN)

( * ) Notice: Subject to any disclaimer, the term of this patent is extended or adjusted under 35 U.S.C. 154(b) by 465 days.

(21) Appl. No.: 16/999,088

(22) Filed: Aug. 21, 2020

(65) Prior Publication Data
US 2021/0055306 A1 Feb. 25, 2021

(30) Foreign Application Priority Data
Aug. 22, 2019 (CN) .......................... 201910780061.7

(51) Int. Cl.
*A61K 39/00* (2006.01)
*G01N 33/574* (2006.01)
*G01N 33/68* (2006.01)

(52) U.S. Cl.
CPC .... *A61K 39/0011* (2013.01); *G01N 33/57484* (2013.01); *G01N 33/57492* (2013.01); *G01N 33/6869* (2013.01); *G01N 33/6866* (2013.01); *G01N 2333/11* (2013.01); *G01N 2333/705* (2013.01); *G01N 2469/20* (2013.01)

(58) Field of Classification Search
None
See application file for complete search history.

(56) References Cited

FOREIGN PATENT DOCUMENTS

WO  WO-2014168874 A2 * 10/2014 ......... A61K 39/0011
WO  WO-2019094642 A1 *  5/2019 ............. A61K 35/15

OTHER PUBLICATIONS

Skolnick et al (Trends Biotechnol. Jan. 2000;18(1):34-9) (Year: 2000).*
Burgess et al. (J. Cell Biol. 111:2129-2138, 1990) (Year: 1990).*
Lazar et al. (Mol. Cell. Biol., 8:1247-1252, 1988) (Year: 1988).*
Miosge (Proc Natl Acad Sci U S A. Sep. 15, 2015;112(37):E5189-98) (Year: 2015).*
Mateu et al. (Mateu MG, et. al. Eur J Immunol. Jun. 1992;22(6):1385-9.) (Year: 1992).*
Greenspan et al. (Greenspan NS, Di Cera E. Defining epitopes: It's not as easy as it seems. Nat Biotechnol. Oct. 1999;17(10):936-7.) (Year: 1999).*
Vajdos et al. (J Mol Biol. Jul. 5, 2002;320(2):415-28 at 416) (Year: 2002).*
Brown et al. (J Immunol. May 1996; 156(9):3285-91 ) (Year: 1996).*
Guido et al (Curr Med Chem. 2008; 15(1):37-46) (Year: 2008).*
Clark et al (J. Med. Chem., 2014, 57 (12), pp. 5023-5038) (Year: 2014).*
Mobs et al.(Journal of Investigative Dermatology, vol. 136, Issue 6, Jun. 2016, pp. e55-e59) (Year: 2016).*
Strobel et al (Gene Therapy (2000) 7, 2028-2035) (Year: 2000).*
NCBI Accession NP_056664.1, downloaded on Aug. 4, 2023 from https://www.ncbi.nlm.nih.gov/protein/NP_056664.1 (Year: 2023).*

\* cited by examiner

*Primary Examiner* — Brian Gangle
*Assistant Examiner* — Andrea K McCollum
(74) *Attorney, Agent, or Firm* — Bayramoglu Law Offices LLC

(57) ABSTRACT

A method and a platform for detecting an immunogenicity of a tumor neoantigen are provided. Specifically, the detection method includes the following steps: culturing human peripheral blood monocytes ex vivo for 13 days, adding an antigenic peptide fragment of human influenza virus and stimulating and activating cytokines, antigenic peptides, and immunoadjuvants during the 13 days, and finally conducting enzyme-linked immunospot (ELISPOT) chromogenic reaction and instrument-based scanning, counting, and analysis to detect the immunogenicity of tumor neoantigen. An application of the detection method and platform in biomedicine is provided. Compared with the prior art, the detection method and platform have advantages and characteristics of a short detection period, high convenience, low consumption of experimental cells, and low detection cost. Therefore, the detection method and platform can be used for ex vivo high-throughput assay for the immunogenicity of the tumor neoantigen.

5 Claims, 2 Drawing Sheets

Specification includes a Sequence Listing.

METHOD AND PLATFORM FOR DETECTING IMMUNOGENICITY OF TUMOR NEOANTIGEN

CROSS REFERENCE TO THE RELATED APPLICATIONS

This application is based upon and claims priority to Chinese Patent Application No. 201910780061.7, filed on Aug. 22, 2019, the entire contents of which are incorporated herein by reference.

TECHNICAL FIELD

The present invention relates to the technical fields of cell culture and immunogenicity assay, and in particular to a method and platform for detecting an immunogenicity of a tumor neoantigen. Specifically, the detection method includes the following steps: culturing human peripheral blood monocytes ex vivo for 13 days, adding an antigenic peptide fragment of human influenza virus and stimulating and activating cytokines and immunoadjuvants during the 13 days, and finally conducting enzyme-linked immunospot (ELISPOT) chromogenic reaction and instrument-based scanning, counting, and analysis to detect the immunogenicity of tumor neoantigen. The present invention further relates to an application of the detection method and platform in biomedicine.

BACKGROUND

Enzyme-linked immunospot (ELISPOT) assay was invented in 1983. With the combination of Western blotting and enzyme-linked immunosorbent assay (ELISA), the ELISPOT assay can detect cytokines secreted at the single-cell level. So far, in the field of medical research and clinical diagnosis, the ELISPOT assay has been used to detect cell-secreted special factors, including cytohormones or chemokines, and can provide both quantitative (activated cell number) and qualitative (types of factors secreted) information.

Different from ELISA, ELISPOT assay is realized by culturing cells in a Petri dish and detecting secretions of each cell directly. Therefore, the ELISPOT assay is used to determine the frequency of cell reaction, but not to detect the overall concentration of a target compound in a lysate. The ELISPOT assay is one of the most sensitive existing ex vivo cell detection techniques, and can detect one activated cell from 200,000 to 300,000 cells, which is extremely suitable for detecting a small number of special cells in immune response due to its high sensitivity. The ELISPOT assay also features high efficiency and high-throughput automation in the process of result reading. However, the ELISPOT assay still has numerous limitations, such as excessively long detection period (usually for weeks), large consumption of experimental cells, and poor convenience of detection. The above disadvantages limit the promotion and use thereof in the field of biomedicine.

SUMMARY

To overcome the above disadvantages of enzyme-linked immunospot (ELISPOT) assay to enable its application in immunogenicity assay for tumor neoantigen, the present invention establishes a stable and reliable standardized ELISPOT platform by using a human influenza virus peptide fragment (a sequence fragment at positions 58-66 of a sequence of Influenza Matrix Protein M1 having) and phytohemagglutinin (PHA) as positive controls to stimulate human peripheral blood monocytes (PBMCs). With a series of controlled trials, a standard operating procedure of the optimal result is finally obtained by comparing different cell culture conditions repeatedly, including cell numbers, different immunoadjuvants, different dendritic cell differentiation time points, different treatment combinations of cytokines, different ex vivo culture stimulation durations, and different ex vivo culture final resting stage durations.

To achieve the above objective, in one aspect, the present invention provides a method for detecting an immunogenicity of a tumor neoantigen, including the following steps:

(1) day 1: culturing $5 \times 10^5$ thawed human PBMCs in a 24-well plate containing 500 µl of a Roswell Park Memorial Institute (RPMI) complete medium in each well, adding 20 ng/ml of human interleukin (IL)-4 and 100 ng/ml of granulocyte-macrophage colony-stimulating factor (GM-CSF), and incubating in a cell incubator for 48 h at 37° C.;

(2) day 3: adding different concentrations of an antigenic peptide fragment of a human influenza virus, 5 ng/ml of human IL-7, and 20 µg/ml of polyinosinic-polycytidylic acid (Poly I:C) into the cell culture medium;

(3) day 5: adding 500 µl of RPMI complete medium supplemented with 10 ng/ml of human IL-7, 10 ng/ml of human IL-15 and 40 U/ml of human IL-2 into each well of the 24-well plate to reach a total volume of 1 ml;

(4) day 8: changing the cell culture medium every three days, including: removing 500 µl of the stale culture medium, and adding 500 µl of a fresh RPMI complete medium supplemented with 10 ng/ml of human IL-7, 10 ng/ml of human IL-15 and 40 U/ml of human IL-2;

(5) day 11: collecting all non-adherent cells from the 24-well plate, washing with the RPMI complete medium twice, and culturing the cells in 500 µl of an RPMI complete medium without any cytokine or stimulating factor for 48 h, to obtain human PBMC-derived T lymphocytes; and (6) day 13: taking out an enzyme-linked immunospot (ELISPOT) strip from a kit, adding 200 µl of RPMI complete medium and different concentrations of an antigenic peptide fragment of a human influenza virus, wherein the RPMI complete medium is supplemented with $2 \times 10^5$ thawed human PBMCs and the $1 \times 10^5$ human PBMC-derived T lymphocytes; mixing uniformly, incubating in the cell incubator for 22 h at 37° C., and subsequently conducting an ELISPOT assay.

Further, the RPMI complete medium in steps (1) and (6) of the detection method is supplemented with 10% (v/v) heat inactivated human serum AB, 100 U/ml penicillin/streptomycin, 2 mM glutamine, 1 mM sodium pyruvate, 0.1 mM non-essential amino acids, 10 mM 2-[4-(2-hydroxyethyl)-1-piperazinyl]ethanesulfonic acid (HEPES), 2.5 µg/ml amphotericin B, and 0.05 mM 2-mercaptoethanol.

Further, the antigenic peptide fragment of the human influenza virus in step (2) of the detection method is a sequence fragment at positions 58-66 of a sequence of Influenza Matrix M1, and the different concentrations include 0.25 ng/ml, 1 ng/ml, and 2 ng/ml, respectively.

Further, the antigenic peptide fragment of the human influenza virus in step (6) of the detection method is a sequence fragment at positions 58-66 of a sequence of Influenza Matrix M1, and the different concentrations include 0.25 ng/ml, 1 ng/ml, and 2 ng/ml, respectively.

The present invention further relates to an application of the detection method in constructing a high-throughput verification system of an immunogenicity of a tumor neoantigen.

The present invention further relates to an application of the detection method in biomedicine.

In another aspect, the present invention provides a platform for detecting an immunogenicity of a tumor neoantigen, wherein the detection platform includes the following components:

(1) an RPMI complete medium;
(2) cytokines and stimulating factors;
(3) Poly I:C;
(4) an antigenic peptide fragment of a human influenza virus; and
(5) an ELISPOT reader system.

Further, the cytokines and the stimulating factors in the detection platform include human IL-2, human IL-4, human IL-7, human IL-15, and GM-CSF, and the antigenic peptide fragment of the human influenza virus is a sequence fragment at positions 58-66 of a sequence of Influenza Matrix M1.

Further, the RPMI complete medium in the detection platform is supplemented with 10% (v/v) heat inactivated human serum AB, 100 U/ml penicillin/streptomycin, 2 mM glutamine, 1 mM sodium pyruvate, 0.1 mM non-essential amino acids, 10 mM 2-[4-(2-hydroxyethyl)-1-piperazinyl] ethanesulfonic acid (HEPES), 2.5 μg/mL amphotericin B, and 0.05 mM 2-mercaptoethanol.

The present invention further relates to an application of the detection platform in constructing a high-throughput verification system of an immunogenicity of a tumor neoantigen.

Compared with the existing ELISPOT assay for immunogenicity, the detection method and platform of the present invention have the following advantages and characteristics:

(1) Short detection period: The standard operating procedure of the present invention merely takes 14 days (13 days for ex vivo culture and stimulation of human PBMCs and 1 day for ELISPOT assay and analysis). Compared with the long detection period of 16-21 days in some prior art, the present invention shortens the detection period significantly, by at most seven days, thus improving the convenience of the detection.

(2) Low detection cost: The present invention optimizes experimental conditions of ex vivo culture of human PBMCs. Compared with methods in the prior art, the method of the present invention merely uses about 1/10 of the amount of human PBMCs used in the prior art for ex vivo culture and stimulation, greatly reducing the consumption and expenses of experimental materials and significantly lowering the detection cost.

DETAILED DESCRIPTION OF THE EMBODIMENTS

Figure 1:
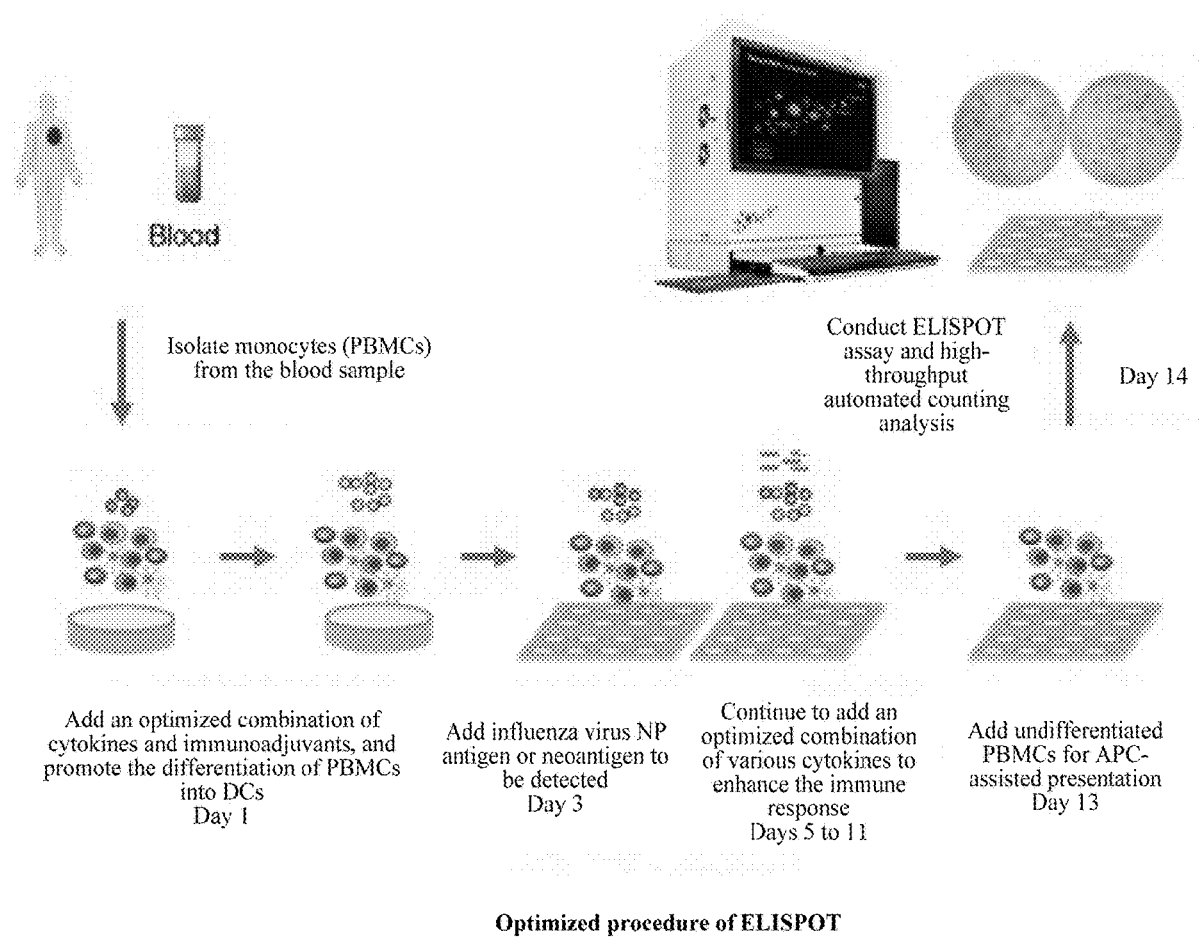
FIG. 1 shows a standard operating procedure of the enzyme-linked immunospot (ELISPOT) platform of the present invention. The standard operating procedure takes 14 days in total, including 13 days for ex vivo culture of human peripheral blood monocytes (PBMCs) (during which a stimulation process of cytokines, antigenic peptides, and immunoadjuvants is carried out) and the last day for ELISPOT chromogenic reaction, counting, and analysis.
Figure 2:
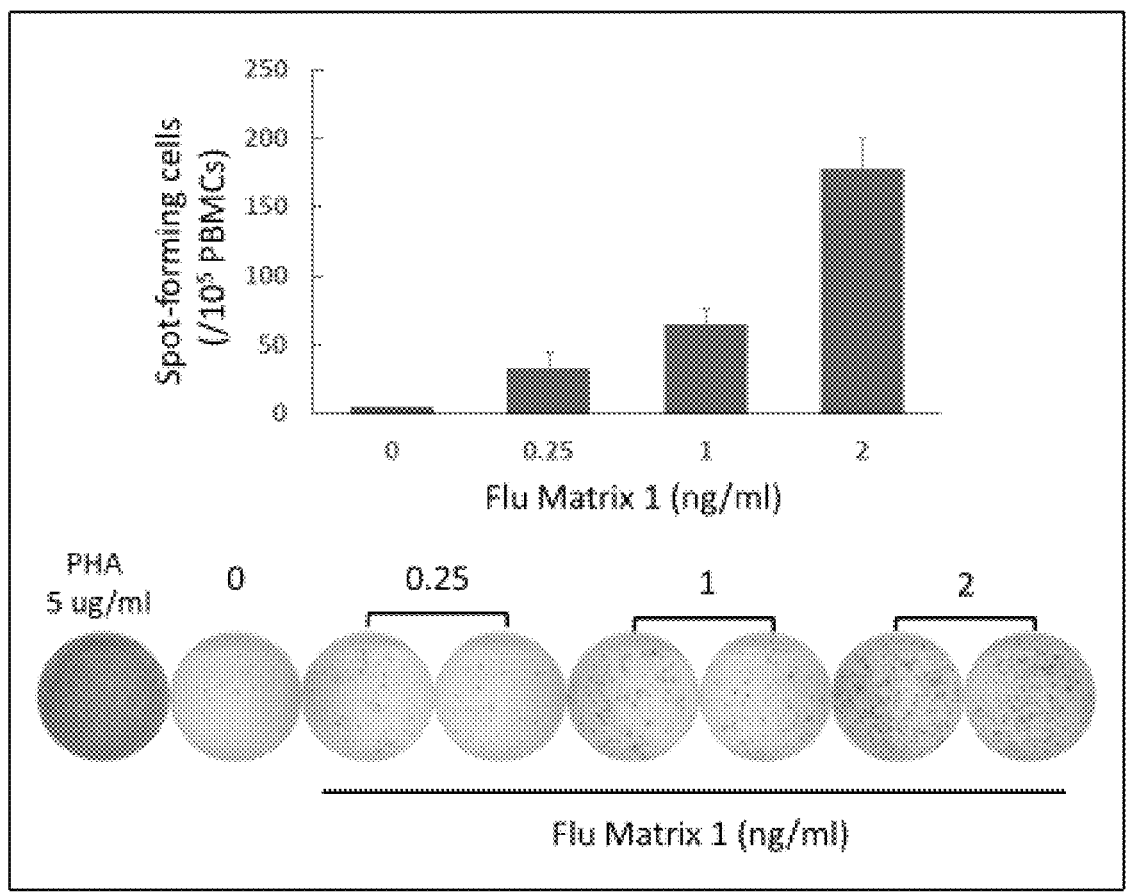
FIG. 2 shows the results of an enzyme-linked immunospot (ELISPOT) platform building experiment. The results are obtained by an ELISPOT assay detection after a reaction of equivalent human peripheral blood monocytes (PBMCs) with different concentrations of a peptide fragment of an influenza virus according to the standard operating procedure. The number of spots finally formed in each well of a Petri dish increases with the increase of the additional amount of the antigenic peptide fragment of the human influenza virus (Influenza Matrix M1), showing a good positive correlation. Thus, a standard curve can be determined. Phytohemagglutinin (PHA) is used as a positive control.

The following describes the present invention in detail through specific embodiments, but it should be noted that the following embodiments are merely exemplary. The present invention can also be implemented or applied through other different embodiments. Based on different viewpoints and applications, various modifications or amendments can be made to the embodiments without departing from the spirit of the present invention.

To enable those skilled in the art to understand the features and effects of the present invention, the following generally describes and defines the terms and dictions mentioned in the specification and claims. Unless otherwise specified, all technical and scientific terms used herein have the same meaning as commonly understood by a person of ordinary skill in the art to which the present invention pertains. In addition to the specific methods, devices, and materials used herein, any method, device, and material equivalent or similar to those described in the embodiments of the present invention can be used to implement the present invention by those skilled in the art according to conventional knowledge and the description of the present invention.

The materials, reagents, etc. used in the following embodiments are all commercially available, unless otherwise specified.

| Embodiments | |
|---|---|
| Reagent used in the experiment | Supplier |
| Human peripheral blood monocytes (PBMCs) | Cellular Technology Limited |
| RPMI 1640 | Sigma-Aldrich |
| Human serum AB | Gemini Bio-Products |
| Penicillin/streptomycin with glutamine | Thermo Fisher Scientific |
| Sodium pyruvate | Thermo Fisher Scientific |
| Non-essential amino acids | Thermo Fisher Scientific |
| 2-[4-(2-Hydroxyerhyl)-1-piperazinyl]ethanesulfonic acid (HEPES) | Thermo Fisher Scientific |
| Amphotericin B | Sigma-Aldrich |
| 2-Mercaptoethanol | Thermo Fisher Scientific |
| Human interleukin-4 (IL-4) | GenScript |
| Granulocyte-macrophage colony-stimulating factor (GM-CSF) | PeproTech |
| Antigenic peptide fragment of human influenza virus (Influenza Matrix M1) | Cellular Technology Limited |
| Human interleukin-7 (IL-7) | PeproTech |
| Polyinosinic-polycytidylic acid (Poly I:C) | Tocris |
| Human interleukin-15 (IL-15) | GenScript |
| Human interleukin-2 (IL-2) | GenScript |
| Human IFN-γ Single-Color ELISPOT Kit | Cellular Technology Limited |

-continued

| Embodiments | |
|---|---|
| | Supplier |
| Device | |
| Immunospot ® S6 ENTRY Analyzer | Cellular Technology Limited |

Embodiment 1: Ex Vivo Culture of Human Peripheral Blood Monocytes (PBMCs)

(1) Day 1: $5\times10^5$ thawed human PBMCs were cultured in a 24-well plate containing 500 µl of an RPMI complete medium (supplemented with 10% (v/v) heat inactivated human serum AB, 100 U/ml penicillin/streptomycin, 2 mM glutamine, 1 mM sodium pyruvate, 0.1 mM non-essential amino acids, 10 mM 2-[4-(2-hydroxyethyl)-1-piperazinyl] ethanesulfonic acid (HEPES), 2.5 µg/mL amphotericin B, and 0.05 mM 2-mercaptoethanol) in each well. The medium had been added 20 ng/ml of human interleukin (IL)-4 and 100 ng/ml of granulocyte-macrophage colony-stimulating factor (GM-CSF) were further added and incubated in a cell incubator for 48 h at 37° C.

(2) Day 3: different concentrations of antigenic peptide fragment of human influenza virus (sequence fragments 58-66 of Influenza Matrix M1; concentrations: 0.25 ng/ml, 1 ng/ml, and 2 ng/ml), 5 ng/ml human IL-7, and 20 µg/ml polyinosinic-polycytidylic acid (Poly I:C) were added into the cell culture medium.

(3) Day 5: 500 µl of an RPMI complete medium (supplemented with 10 ng/ml of human IL-7, 10 ng/ml of IL-15, and 40 U/ml of human IL-2) was added into each well of the 24-well plate to reach a total volume of 1 ml (a final concentration of each of human IL-7 and IL-15 was 5 ng/ml; a final concentration of human IL-2 was 20 U/ml).

(4) Day 8: the cell culture medium was changed every three days. 500 µl of the stale culture medium was removed, and 500 µl of a fresh RPMI complete medium (supplemented with 10 ng/ml of human IL-7, 10 ng/ml of IL-15, and 40 U/ml of human IL-2) was added.

(5) Day 11: all non-adherent cells were collected from the 24-well plate, washed with the RPMI complete medium twice, and cultured in 500 µl of an RPMI complete medium without any cytokine and stimulating factor for 48 h, to obtain human PBMC-derived T lymphocytes.

(6) Day 13: an enzyme-linked immunospot (ELISPOT) strip was taken out from a kit and mounted on the strip plate of the kit. After placing for warming, 200 µl of an RPMI complete medium (supplemented with $2\times10^5$ thawed human PBMCs and $1\times10^5$ human PBMC-derived T lymphocytes) and different concentrations of an antigenic peptide fragment of a human influenza virus (a sequence fragment at positions 58-66 of a sequence of Influenza Matrix M1; the different concentrations includes 0.25 ng/ml, 1 ng/ml, and 2 ng/ml) were added, mixed uniformly, incubated in the cell incubator for 22 h at 37° C., and subsequently subjected to an ELISPOT assay.

Embodiment 2: ELISPOT Chromogenic Reaction

Day 14: The ELISPOT strip plate placed in the cell incubator for 22 h was taken out. The cells and cell culture medium therein were discarded. The remaining steps were implemented with reference to the operating instructions of the Human IFN-γ Single-Color ELISPOT Kit:

(1) washing the ELISPOT strip plate twice with phosphate-buffered saline (PBS) and 0.05% Tween-PBS (the volume was 200 µl per well), respectively;

(2) adding anti-human IFN-γ detection solution (the volume was 80 µl per well), mixing uniformly, and keeping for 2 h at room temperature;

(3) washing the ELISPOT strip plate thrice with 0.05% Tween-PBS (the volume was 200 µl per well)

(4) adding tertiary detection solution (the volume was 80 µl per well), mixing uniformly, and keeping for 30 min at room temperature;

(5) washing the ELISPOT strip plate twice with 0.05% Tween-PBS and distilled water (the volume was 200 µl per well), respectively;

(6) adding chromogen solution (the volume was 80 µl per well), mixing uniformly, and placing in the dark for 15 min at room temperature;

(7) adding sufficient tap water to stop the chromogenic reaction, taking out the ELISPOT strip from the strip plate, and drying at room temperature; and (8) scanning and analyzing the number of immunospots in each well of the Petri dish by Immunospot® S6 ENTRY Analyzer.

The specific implementations and embodiments of the present invention are described in detail above, but the present invention is not limited to the above implementations and embodiments. Within the knowledge of a person of ordinary skill in the art, various modifications can further be made without departing from the spirit of the present invention.

What is claimed is:

1. A system for detecting an immunogenicity of a tumor neoantigen, comprising the following components:
    (1) a Roswell Park Memorial Institute (RPMI) medium comprising 10% (v/v) heat inactivated human serum AB, 100 U/ml penicillin, 100 U/ml streptomycin, 1 mM sodium pyruvate, 0.1 mM non-essential amino acids, 10 mM 2-[4-(2-hydroxyethyl)-1-piperazinyl]ethanesulfonic acid (HEPES), 2.5 μg/ml amphotericin B, and 0.05 mM 2-mercaptoethanol;
    (2) cytokines;
    (3) polyinosinic-polycytidylic acid (Poly I:C);
    (4) an antigenic peptide fragment of a human influenza; and
    (5) an enzyme-linked immunospot (ELISPOT) Reader.

2. The system according to claim 1, wherein the cytokines comprise one or more of human interleukin (IL)-2, human IL-4, human IL-7, human IL-15, or granulocyte-macrophage colony-stimulating factor (GM-CSF).

3. A method for detecting an immunogenicity of a tumor neoantigen, comprising:
    adding human interleukin (IL)-4 into a first Roswell Park Memorial Institute (RPMI) medium comprising 10% (v/v) heat inactivated human serum AB, 100 U/ml penicillin, 100 U/ml streptomycin, 1 mM sodium pyruvate, 0.1 mM non-essential amino acids, 10 mM 2-[4-(2-hydroxyethyl)-1-piperazinyl]ethanesulfonic acid (HEPES), 2.5 μg/ml amphotericin B, and 0.05 mM 2-mercaptoethanol to obtain a first culture solution having an IL-4 concentration of 20 ng/ml;
    adding granulocyte-macrophage colony-stimulating factor (GM-CSF) into the first culture solution, to obtain a second culture solution having a GM-CSF concentration of 100 ng/ml;
    culturing $5 \times 10^5$ thawed human peripheral blood monocytes (PBMCs) in a 24-well plate containing 500 μl of the second culture solution per well and incubating the second culture solution containing PBMCs for 48 h at 37° C.;
    adding human IL-7, polyinosinic-polycytidylic acid (Poly I:C), and a first antigenic peptide fragment of a human influenza virus into the second culture solution containing PBMCs to obtain a third culture solution having a human IL-7 concentration of 5 ng/ml and a Poly I:C concentration of 20 μg/ml;
    adding a second RPMI medium comprising 10 ng/ml of human IL-7, 10 ng/ml of IL-15, and 40 U/ml of human IL-2 into each well of the 24-well plate to obtain a fourth culture solution containing PBMCs, wherein the total volume of the fourth culture solution containing PBMCs per well is 1 ml;
    replacing 500 μl of the fourth culture solution with 500 μl of RPMI medium comprising 10 ng/ml of human IL-7, 10 ng/ml of IL-15, and 40 U/ml of human IL-2;
    collecting non-adherent PBMCs from the 24-well plate, washing the non-adherent cells with RPMI medium twice, and then culturing the non-adherent cells in RPMI medium without any cytokines for 48 h, to obtain human PBMC-derived T lymphocytes;
    combining 200 μl of RPMI medium comprising 10% (v/v) heat inactivated human serum AB, 100 U/ml penicillin, 100 U/ml streptomycin, 1 mM sodium pyruvate, 0.1 mM non-essential amino acids, 10 mM 2-[4-(2-hydroxyethyl)-1-piperazinyl]ethanesulfonic acid (HEPES), 2.5 μg/ml amphotericin B, 0.05 mM 2-mercaptoethanol, $2 \times 10^5$ thawed human PBMCs, $1 \times 10^5$ cells of the human PBMC-derived T lymphocytes, and a second antigenic peptide fragment of a human influenza virus to obtain a fifth culture solution; and
    conducting an ELISPOT assay on the fifth culture solution.

4. The method according to claim 3, wherein the concentration of the first antigenic peptide fragment of a human influenza virus is 0.25 ng/ml, 1 ng/ml, or 2 ng/ml.

5. The method according to claim 3, wherein the concentration of the second antigenic peptide fragment of a human influenza virus is 0.25 ng/ml, 1 ng/ml, or 2 ng/ml.

* * * * *

SEQUENCE LISTING

<160> NUMBER OF SEQ ID NOS: 1

<210> SEQ ID NO 1
<211> LENGTH: 9
<212> TYPE: PRT
<213> ORGANISM: Influenza A virus

<400> SEQUENCE: 1

Gly Ile Leu Gly Phe Val Phe Thr Leu
1               5